United States Patent
Flöter et al.

(10) Patent No.: US 10,857,255 B2
(45) Date of Patent: Dec. 8, 2020

(54) ABSORBENT CORE WRAP WITH A LOW BASIS WEIGHT NONWOVEN IN THE BOTTOM LAYER

(71) Applicant: The Procter & Gamble Company, Cincinnati, OH (US)

(72) Inventors: Stefan Flöter, Euskirchen (DE); Geeske Gratzel, Euskirchen (DE); Torsten Lindner, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 379 days.

(21) Appl. No.: 15/907,374

(22) Filed: Feb. 28, 2018

(65) Prior Publication Data

US 2018/0256772 A1 Sep. 13, 2018

(30) Foreign Application Priority Data

Mar. 9, 2017 (EP) ..................... 17160193

(51) Int. Cl.
*A61F 13/15* (2006.01)
*A61L 15/20* (2006.01)
(Continued)

(52) U.S. Cl.
CPC ........ *A61L 15/20* (2013.01); *A61F 13/15203* (2013.01); *A61F 13/15634* (2013.01); *A61F 13/15674* (2013.01); *A61F 13/535* (2013.01); *A61F 13/53704* (2013.01); *A61F 13/53756* (2013.01); *A61F 13/84* (2013.01); *A61L 15/50* (2013.01); *D04H 3/007* (2013.01); *D04H 3/16* (2013.01); *D04H 5/00* (2013.01); *A61F 2013/15406* (2013.01);
(Continued)

(58) Field of Classification Search
CPC .... A61L 15/20; A61L 15/50; A61F 13/15203; A61F 13/15634; A61F 13/15674; A61F 13/535; A61F 13/53704; A61F 13/53756; A61F 13/84; A61F 2013/530379; A61F 2013/530489; A61F 2013/5315; D04H 3/007; D04H 3/16; D04H 5/00
USPC .... 604/367, 370, 372, 378, 385.23, 385.101
See application file for complete search history.

(56) References Cited

U.S. PATENT DOCUMENTS 6,740,609 B1  5/2004  Peng et al.
2003/0157859 A1  8/2003  Ishikawa
(Continued)

FOREIGN PATENT DOCUMENTS

EP  1298240  4/2003
WO  WO 2015/075632  5/2015

OTHER PUBLICATIONS

European Search Report, dated Jul. 8, 2017, Appln. No. 17160193.3-1308.
(Continued)

*Primary Examiner* — Jacqueline F Stephens
(74) *Attorney, Agent, or Firm* — Christian M. Best (57) ABSTRACT

An absorbent article includes an absorbent core having an absorbent material enclosed in a core wrap having a top layer and a bottom layer. The bottom layer of the core wrap comprises a nonwoven comprising synthetic fibers, which has a basis weight from about 6 $g/m^2$ to about 10 $g/m^2$ and the nonwoven has a static coefficient of friction as measured in cross-machine direction of no more than 0.40.

18 Claims, 6 Drawing Sheets

(51) Int. Cl.
      *D04H 3/16*         (2006.01)
      *D04H 5/00*         (2012.01)
      *D04H 3/007*       (2012.01)
      *A61L 15/50*       (2006.01)
      *A61F 13/537*      (2006.01)
      *A61F 13/535*      (2006.01)
      *A61F 13/84*       (2006.01)
      *A61F 13/531*      (2006.01)
      *A61F 13/53*       (2006.01)
      *A61F 13/534*      (2006.01)

(52) U.S. Cl.
      CPC .................. *A61F 2013/5315* (2013.01); *A61F 2013/5349* (2013.01); *A61F 2013/530379* (2013.01); *A61F 2013/530489* (2013.01); *A61F 2013/8455* (2013.01)

(56) References Cited

U.S. PATENT DOCUMENTS

| | | |
|---|---|---|
| 2003/0181112 A1 | 9/2003 | Ishikawa et al. |
| 2004/0033750 A1* | 2/2004 | Everett ............. A61F 13/15203 442/381 |
| 2009/0111347 A1 | 4/2009 | Peng et al. |
| 2016/0251788 A1 | 9/2016 | Huang et al. |

OTHER PUBLICATIONS

International Search Report and Written Opinion, PCT/US2018/19807, dated Apr. 25, 2018.

* cited by examiner

ABSORBENT CORE WRAP WITH A LOW BASIS WEIGHT NONWOVEN IN THE BOTTOM LAYER

CROSS REFERENCE TO RELATED APPLICATION

This application claims priority, under 35 U.S.C. § 119, to Patent Application No. EP 17160193.3, filed on Mar. 9, 2017, which is hereby incorporated by reference in its entirety.

FIELD

The present disclosure relates to absorbent articles for personal hygiene, such as diapers, that comprise an absorbent core having an absorbent material enclosed by a core wrap. The core wrap comprises a top layer and a bottom layer. The bottom layer of the present disclosure comprises a low basis weight nonwoven material having a low coefficient of friction. A slip agent, in particular a fatty acid amide melt additive, may be used to reduce the coefficient of friction of the nonwoven.

BACKGROUND

Absorbent articles for personal hygiene such as diapers for babies or incontinent adults are designed to absorb and contain body exudates, in particular large quantity of urine. These absorbent articles comprise several layers providing different functions, such as a topsheet, a backsheet and in-between an absorbent core, among other layers. The absorbent core should absorb and retain the exudates for a prolonged amount of time in order to keep the wearer dry and avoid soiling of clothes or bed sheets. At the same time, the absorbent core should make the most efficient use possible of the absorbent material to save material costs and keep the diapers as thin as possible.

The majority of currently marketed absorbent articles comprise as absorbent material a blend of cellulose fibers with superabsorbent polymers (SAP) particles, also called absorbent gelling materials (AGM), see for example U.S. Pat. No. 5,151,092 (Buell). Absorbent cores with absorbent material consisting essentially of SAP without cellulose fibers (so called "airfelt-free" cores) have also been proposed. For example WO2008/155699 (Hundorf et al.) discloses absorbent cores with a patterned layer of SAP immobilized by a net of fibrous thermoplastic adhesive material deposited over the layer of SAP. The fibrous thermoplastic material helps maintaining the SAP in position within the absorbent core prior to and during use of the article, without substantially restricting the ability of the SAP to absorb large volumes of urine.

The absorbent material is typically enclosed in a core wrap so that the absorbent core maintains its integrity on the converting line when it is assembled with the other components of the absorbent article and during use of the absorbent article. The core wrap may be formed by any material suitable for receiving and containing the absorbent material. Typical core wrap materials are papers, tissues, films, wovens, nonwovens, and laminate of any of these. The core wrap may in particular be formed by a nonwoven web, such as a carded nonwoven, spunbond nonwoven ("S") or meltblown nonwoven ("M"), and multilayer laminates of these. Spunmelt nonwovens having a multilayer SM, SMS, or SMMS, or SSMMS structure are commonly used. Nonwoven materials provided from synthetic fibers, such as PE, PET and in particular PP, are typically used.

Many core wraps comprise two separate substrates that are attached to another at the edges of the core. The substrate oriented towards the topsheet is referred herein as top layer and the substrate oriented towards the backsheet is herein referred to as bottom layer. It is also possible as an alternative to have a core wrap comprising a single substrate that forms at the same time the top layer and the bottom layer. The present disclosure is applicable to both type of core wrap construction.

The top layer of the core wrap is typically hydrophilic, so that the urine can quickly pass through this top layer and be absorbed by the absorbent material. Nonwoven layers made of synthetic fibers are typically rendered hydrophilic by adding a surfactant at their surface, as is known in the art. The bottom layer may be advantageously more hydrophobic than the top layer, to provide additional barrier properties in addition to the backsheet. Synthetic fibers are typically inherently hydrophobic unless treated as indicated above.

Typical attachments between the core wrap layers are the so-called C-wrap and the sandwich seal. In a C-wrap, the longitudinal and/or transversal edges of one of the layer form flaps that extend beyond the edges of the absorbent material area and are folded over the other layer. These folded flaps are bonded to the external surface of the other layer, typically by gluing. In the sandwich seal, extensions of both layers are attached to each other in a face to face relation at the edge of the core. Both types of attachments may be combined, for example C-wraps on the longitudinal sides of the core and a sandwich seal at the transversal edges. If the core wrap is made of a single substrate, a C-wrap is typically used longitudinally for a single longitudinal seal and optionally a sandwich seal at each of the transversal edges.

It is generally desirable to reduce the manufacturing costs of disposable diapers. One way to reduce cost is to reduce the basis weight of the materials used. It has been however proven difficult to reduce the basis weight of nonwoven core wrap material below about 10 gsm due to irregularities known as wrinkling happening on the converting line, especially taking into account the high speed encountered on modern converting machines. These wrinkles can develop in so-called z-folds that create mistracked web rejects and line stops, especially just before splicing. The present disclosure addresses this problem.

SUMMARY

The present disclosure in a first aspect for an absorbent article is indicated in claim 1. The article comprises a liquid permeable topsheet, a liquid impermeable backsheet, and an absorbent core between the topsheet and the backsheet, wherein the absorbent core comprises an absorbent material enclosed in a core wrap having a top layer and a bottom layer. The bottom layer of the core wrap comprises a nonwoven having a low basis weight of from about 6 g/m$^2$ to about 10 g/m$^2$ and has a static coefficient of friction as measured in cross-machine direction of no more than 0.40. The coefficient of friction is measured according to standard method ASTM D1894-01.

In a second aspect, the present disclosure is directed, in part, to the use of a slip agent having Coefficient of Friction-reducing properties to reduce the occurrence of wrinkles of the nonwoven when the nonwoven is driven between two rollers. In a particular aspect, the slip agent is added as a melt additive to a plastic melt from which the nonwoven fibers are made, and then converting the resulting nonwoven in a continuous process on a converting line into an absorbent core. The nonwoven is used to form the bottom layer of the absorbent core, the absorbent core further comprising an absorbent layer and a top layer, the top layer and the bottom layer forming a core wrap around the absorbent material. The melt additive can be a fatty acid amide, as a single compound or as a blend of different fatty acid amides.

The present disclosure is directed, in part, to an absorbent article having a wearer-facing surface. The absorbent article comprises a liquid permeable topsheet, a liquid impermeable backsheet, and an absorbent core at least partially between the topsheet and the backsheet. The absorbent core comprises an absorbent material enclosed in a core wrap comprising a first layer and a second layer. The first layer is positioned more proximate to the wearer-facing surface than the second layer. The second layer of the core wrap comprises a nonwoven comprising synthetic fibers. The nonwoven has a basis weight from about 6 $g/m^2$ to about 10 $g/m^2$. The nonwoven has a static coefficient of friction as measured in cross-machine direction of no more than 0.40, as measured according to ASTM D1894-01. At least some of the fibers of the nonwoven comprise a slip agent that reduces the coefficient of friction of the nonwoven.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

Various non-limiting forms of the present disclosure will now be described to provide an overall understanding of the principles of the structure, function, manufacture, and use of the absorbent core wrap with a low basis weight nonwoven in the bottom layer disclosed herein. One or more examples of these non-limiting forms are illustrated in the accompanying drawings. Those of ordinary skill in the art will understand that the absorbent core wrap with a low basis weight nonwoven in the bottom layer specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

General Description of an Absorbent Article

Figure 1:
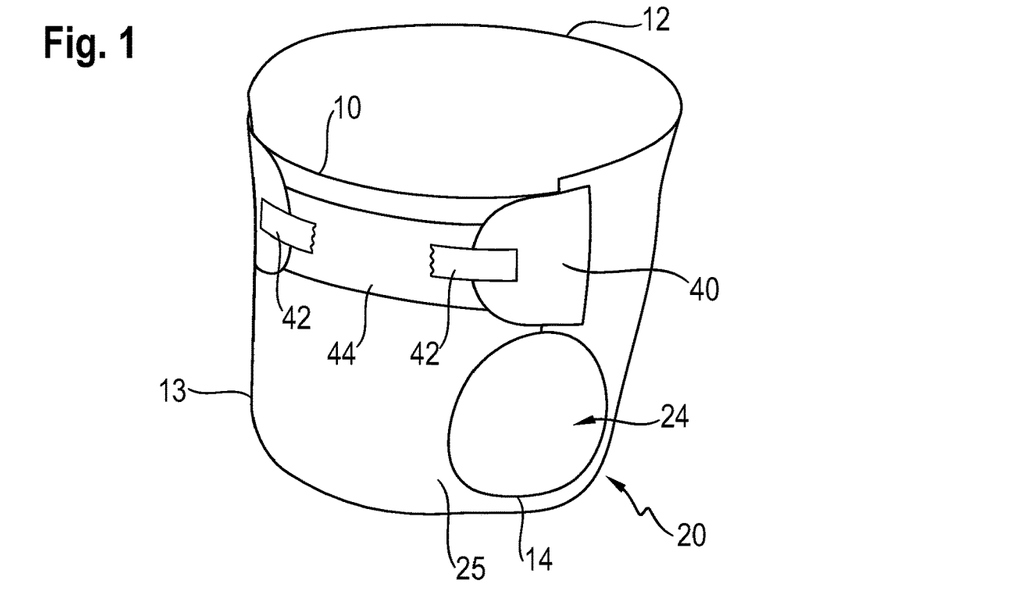
FIG. 1 shows a perspective view of an exemplary taped diaper in a closed configuration as it would be when worn by a wearer.
Figure 2:
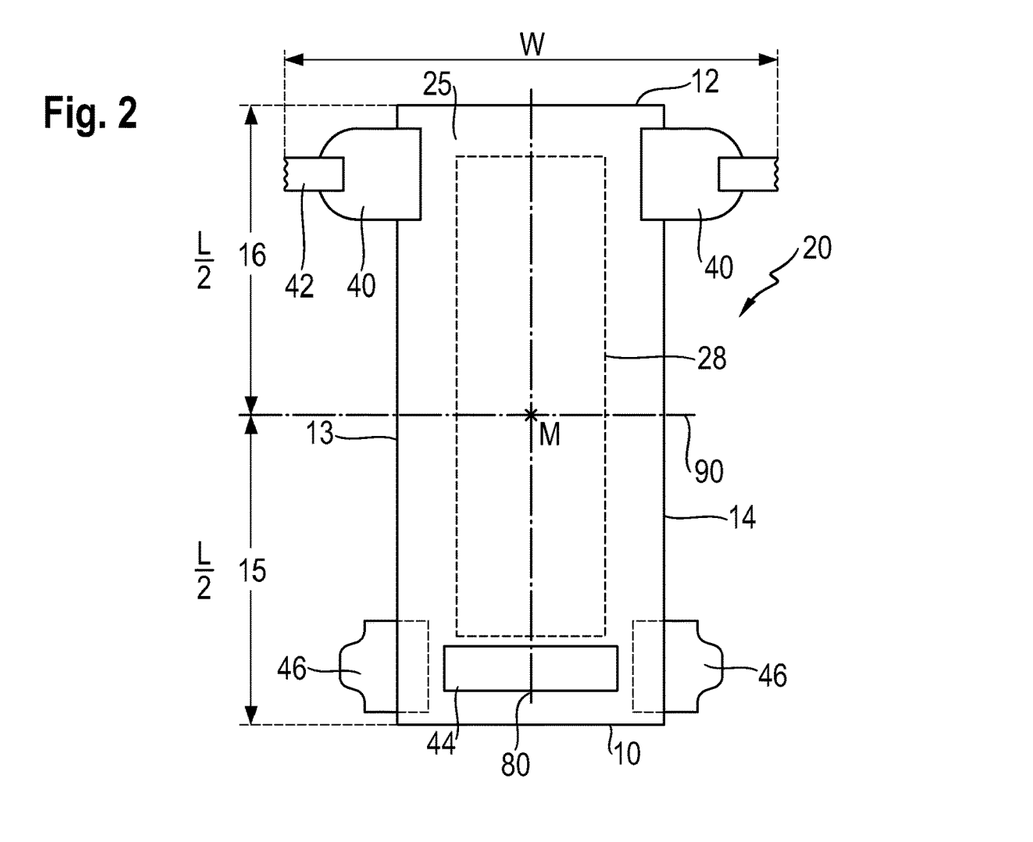
FIG. 2 shows the garment-facing side of the diaper of FIG. 1 with the diaper flattened out.
Figure 3:
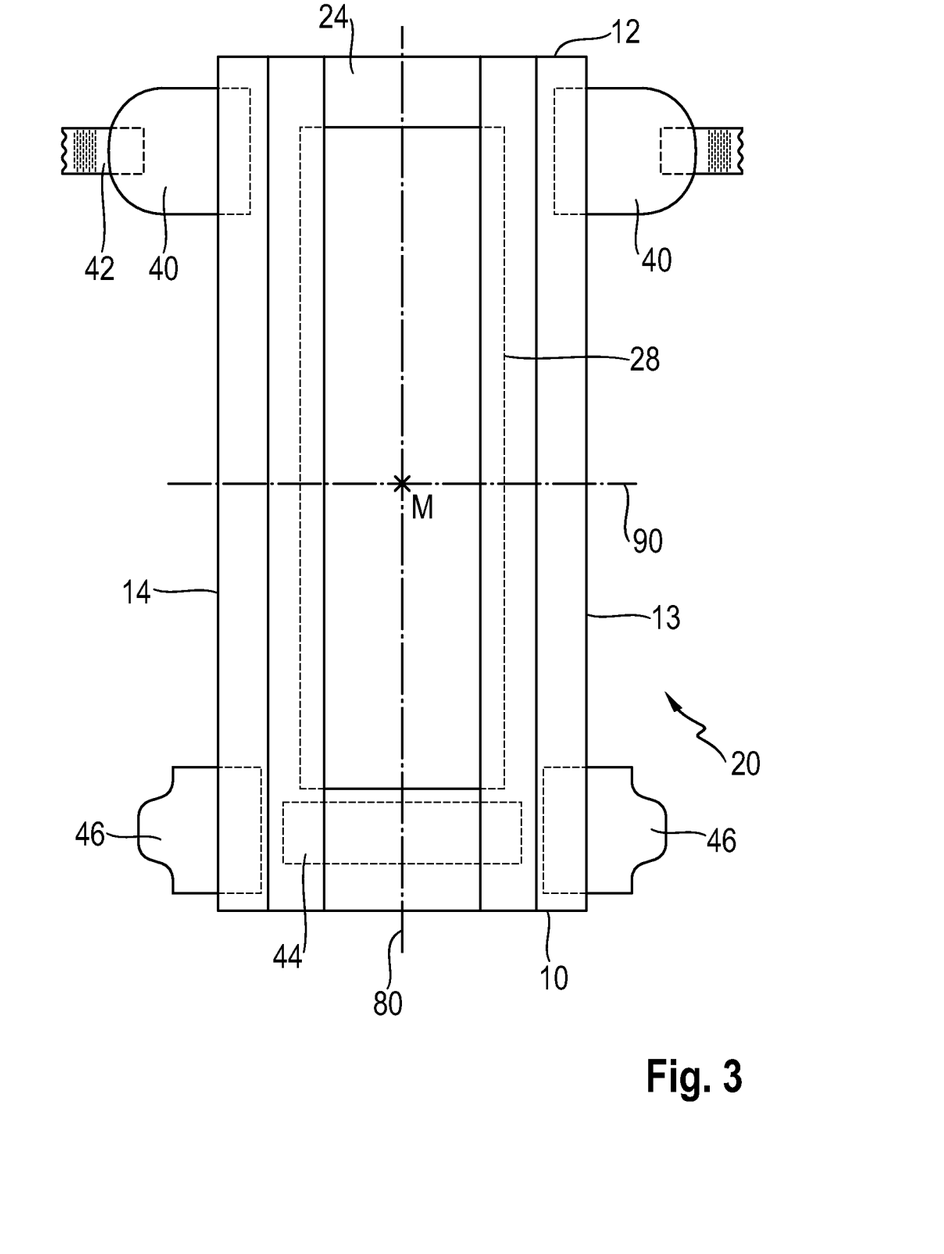
FIG. 3 shows the wearer-facing side of the diaper of FIG. 1 with the diaper flattened out.

An exemplary absorbent article according to the present disclosure in the form of a baby taped diaper 20 is represented in FIGS. 1-3. FIG. 1 is a perspective view of the exemplary diaper in a closed state as it would appear when worn by a wearer. This taped diaper 20 is shown for illustration purpose only as the present disclosure may be used for making a wide variety of diapers or other absorbent articles such as baby diaper pants, adult incontinence pants or feminine sanitary pads. In the following, the word "diaper" and "absorbent article" are used interchangeably. The Figures are used herein as illustration of one way to carry out the present disclosure and are not limiting the scope of the claims, unless specifically indicated to do so.

The absorbent article comprises a liquid permeable topsheet 24 on its wearer-facing surface, a liquid impermeable backsheet 25 on its garment-facing surface and an absorbent core 28 between the topsheet and the backsheet (shown in dotted line in FIG. 2). The topsheet typically forms the majority of the wearer-contacting surface of the article and is the first layer that the body exudates contact. The topsheet is liquid permeable, permitting liquids to readily penetrate through its thickness. Any known topsheet may be used in the present disclosure. The backsheet typically comprises a fluid impermeable plastic film, which may be printed with a backsheet pattern, and a low basis weight nonwoven cover glued to this impermeable film to give a nicer feel and appearance to the backsheet.

The absorbent article may also comprise a fluid acquisition layer and/or a fluid distribution layer between the topsheet and the absorbent core and other typical diaper components such as elasticized gasketing cuffs, upstanding barrier leg cuffs, which are not represented for simplicity but are present in most diapers. The absorbent article may also comprise other usual components if it is desired to increase the performance of the article, such as transverse barrier cuffs, front and/or back elastic waistbands, a lotion application on the topsheet, longitudinally extending channels in the core and/or the distribution layer, a wetness indicator, etc. . . . all these components have been described and exemplified in the art and are not further detailed herein. More detailed disclosures of example of such components are for example disclosed in WO201493323, WO2015/183669 (both Bianchi et al), WO 2015/031225 (Roe et al.) or WO2016/133712 (Ehrnsperger et al.) to name a few.

The absorbent article typically comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The topsheet 24, the backsheet 25, the absorbent core 28 and the other article components may be assembled in a variety of well-known configurations, in particular by gluing, fusion and/or pressure bonding. The absorbent articles of the present disclosure may comprises any typical layers and components used in absorbent products of the diaper type, and which are not necessarily represented in the simplified FIGS. 1-3.

General Description of an Absorbent Core

Figure 4:
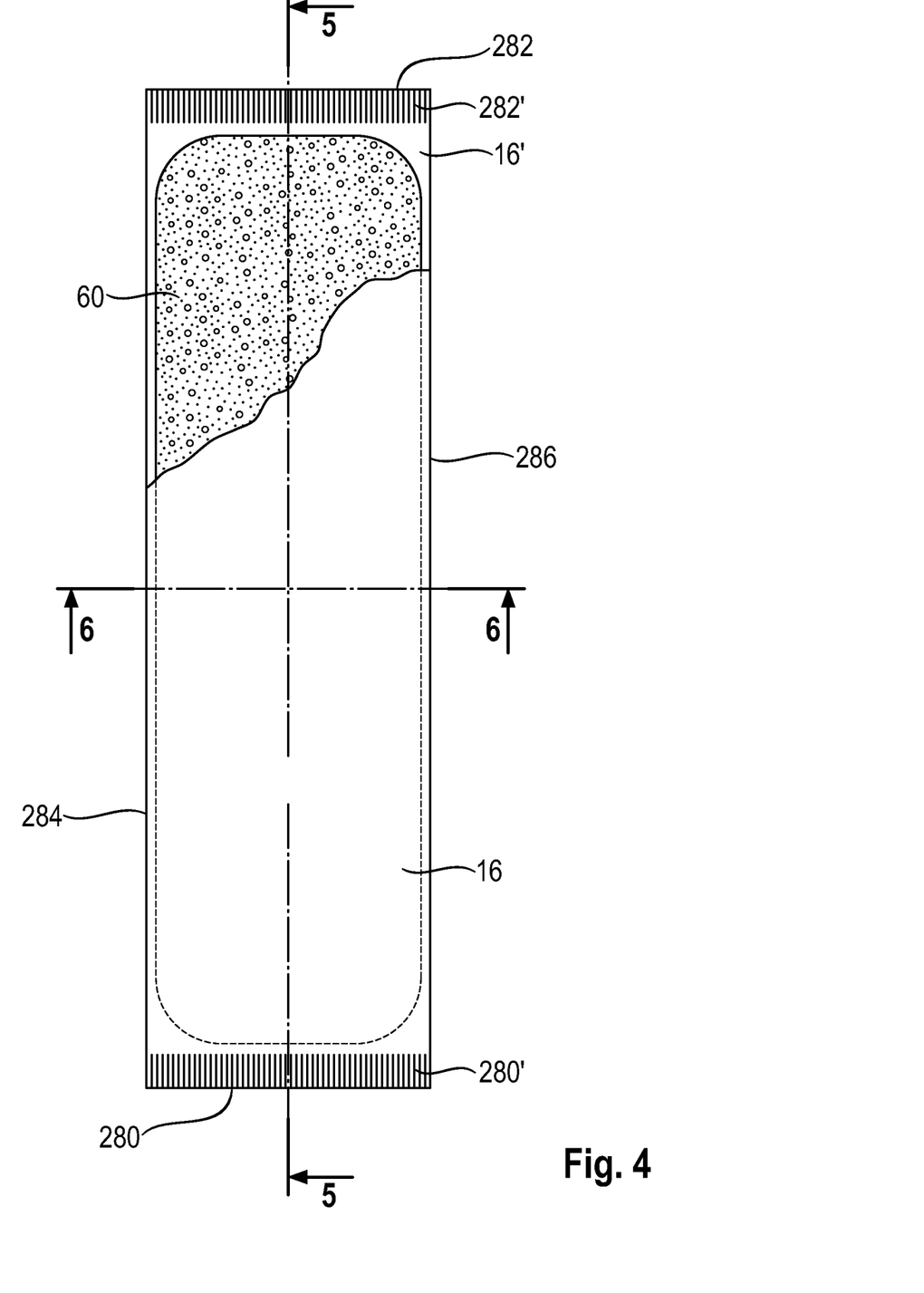
FIG. 4 shows a top view of an exemplary absorbent core with the top layer partially removed.

The absorbent core is the component of the absorbent article having the most absorbent capacity. An exemplary absorbent core 28 is shown in isolation in FIGS. 4-6, in dry state (before use). The absorbent core represented has a generally rectangular shape as defined by the longitudinal edges 284, 286 and transversal front edge 280 and back edge 282. The periphery of the layer formed by the absorbent material 60 within the core wrap, as seen from the top side of the absorbent core, can be generally rectangular, for example as shown in FIG. 4. This absorbent core represented is of course not limiting the scope of the present disclosure as the present disclosure is applicable to a wide variety of absorbent cores. Other shapes can also be used such as a "T" or "Y" or "sand-hour" or "dog-bone" shape for the area of the absorbent material. In particular the area of absorbent material may define a tapering along its width towards the middle region of the core. In this way, the absorbent material deposition area may have a relatively narrow width in an area of the core intended to be placed in the crotch region of the absorbent article. This may provide for example better wearing comfort.

The absorbent material 60 may be any conventional absorbent material known in the art. For example the absorbent material may comprise a blend of cellulose fibers and superabsorbent particles ("SAP"), typically with the percentage of SAP ranging from 40% to 70% by weight of the absorbent material. The absorbent material may also be free of cellulose fibers, as is known in so-called airfelt-free cores where the absorbent material consists of SAP. "Superabsorbent polymers" or "SAP" as used herein refer to absorbent material which are cross-linked polymeric materials that can absorb at least 10 times, optionally at least 15 times, their weight of an aqueous 0.9% saline solution as measured using the Centrifuge Retention Capacity (CRC) test (EDANA method WSP 241.2-05E). These polymers are typically used in particulate forms so as to be flowable in the dry state. The term "particles" refers to granules, fibers, flakes, spheres, powders, platelets and other shapes and forms known to persons skilled in the art of superabsorbent polymer particles.

Various absorbent core designs comprising high amount of SAP have been proposed in the past, see for example in U.S. Pat. No. 5,599,335 (Goldman), EP1,447,066 (Busam), WO95/11652 (Tanzer), US2008/0312622A1 (Hundorf), WO2012/052172 (Van Malderen). In particular the SAP printing technology as disclosed in US2006/024433 (Blessing), US2008/0312617 and US2010/0051166A1 (both to Hundorf et al.) may be used. The present disclosure is however not limited to a particular type of absorbent core. The absorbent core may also comprise one or more glue such as auxiliary glue applied between the internal surface of one (or both) of the core wrap layers and the absorbent material to reduce leakage of SAP outside the core wrap. A micro-fibrous adhesive net may also be used in air-felt free cores as described in the above Hundorf references. These glues are not represented in the Figures for simplicity.

The absorbent material may be for example deposited as a continuous layer within the core wrap. The absorbent material may also be present discontinuously for example as individual pockets or stripes of absorbent material enclosed within the core wrap and separated from each other by material-free junction areas. A continuous layer of absorbent material, in particular of SAP, may also be obtained by combining two absorbent layers having matching discontinuous absorbent material application pattern wherein the resulting layer is substantially continuously distributed across the absorbent particulate polymer material area. As for example taught in US2008/0312622A1 (Hundorf), each absorbent material layer may thus comprise a pattern having absorbent material land areas and absorbent material-free junction areas, wherein the absorbent material land areas of the first layer correspond substantially to the absorbent material-free junction areas of the second layer and vice versa.

Figures 5, 6:
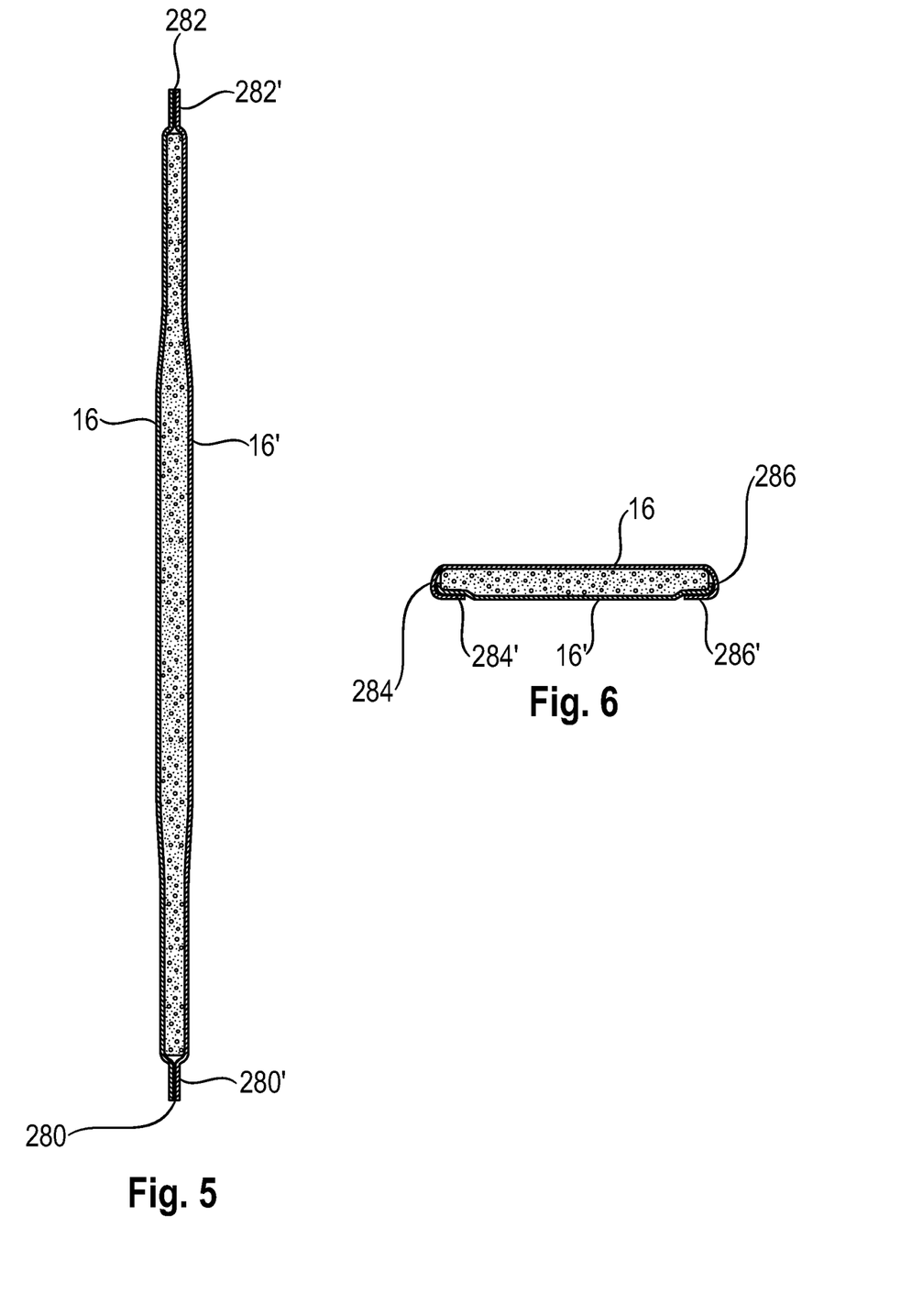
FIG. 5 shows a longitudinal cross-section view of the absorbent core of FIG. 4.
FIG. 6 shows transversal cross-section view of the absorbent core of FIG. 4.

The basis weight (amount deposited per unit of surface) of the absorbent material may also be varied to create a profiled distribution of absorbent material, in particular in the longitudinal direction (as schematically illustrated in FIG. 5) to provide more absorbency towards the center and the middle of the core, but also in the transversal direction, or both directions of the core. The absorbent core may also comprise longitudinally extending channels which are substantially free of absorbent material within the absorbent material area. The core wrap may be bonded through these material-free areas. Exemplary disclosures of such channels in an airfelt-free core can be found in WO2012/170778 (Rosati et al.) and US2012/0312491 (Jackels). Channels may of course also be formed in absorbent cores comprising cellulose fibers.

Core Wrap

The function of the core wrap is to enclose the absorbent material. As indicated in the background, different core wrap constructions can be used. Typical core wraps comprise two substrates 16, 16' which are attached to another and form respectively the top layer and the bottom layer of the core wrap. These two layers may be typically attached to another along at least part of the periphery of the absorbent core to form a seal. Typically neither the first nor the second substrate needs to be shaped, so that they can be rectangularly cut for ease of production but other shapes are not excluded. The terms "seal" and "enclosing" are to be understood in a broad sense. The seal does not need to be continuous along the whole periphery of the core wrap but may be discontinuous along part or the whole of it, such as formed by a series of seal points spaced on a line. Typically a seal may be formed by gluing and/or thermal bonding.

The core wrap represented in the Figures comprises a top layer 16 which is wider than the bottom layer 16' so that two flaps of the top layer can be folded over the bottom layer along the longitudinal edges 284, 286 of the core respectively to which they are attached, typically by an adhesive to form the longitudinal seals 284', 286'. The front edge 280 and back edge 282 may also be sealed, for example by a sandwich seal 280', 282'. Such transversal seals may for example made by adhesive stripes applied by the slot glue technique, as is known in the art. Alternatively, is it possible to leave the transversal edges 280, 282 open without a seal. For example there may be enough core wrap material between the edges of the core and the absorbent material 60 to provide a buffer zone at these ends.

The top layer and the bottom layer may be made from the same base substrate material which has been differently treated. As indicated in the background, the top layer may be typically a nonwoven layer made of synthetic fibers that has been treated with a surfactant to increase its hydrophilicity. Hydrophilicity and wettability are typically defined in terms of contact angle and the strike through time of the fluids. This is discussed in detail in the American Chemical Society publication entitled "Contact angle, wettability and adhesion", edited by Robert F. Gould (Copyright 1964). A substrate having a lower contact angle between water and its surface is more hydrophilic than another having a higher contact angle. Generally, if the water contact angle is smaller than 90°, the substrate is considered hydrophilic and if the water contact angle is larger than 90°, the substrate is considered hydrophobic. The contact angle values can be measured on the fibers at the surface of the nonwoven using a SEM microscope as indicated in the experimental section below.

The bottom layer and top layer may be made of a similar type of nonwoven, but with a different treatment to provide the different desired properties. Both layers may in particular each comprises or consists of a nonwoven web, such as a carded nonwoven, a spunbond nonwoven ("S") or a meltblown nonwoven ("M"), and a multi-layer of any of these. For example spunbond/meltblown laminate (spunmelt) polypropylene nonwovens are commonly used and are particularly suitable, especially those having a multi-layer SMS, or SMMS, or SSMMS, structure. Examples are disclosed in U.S. Pat. No. 7,744,576, US2011/0268932A1, US2011/0319848A1 or US2011/0250413A1. Typical material used to make the synthetic fibers are PE (polyethylene), PET (polyethylene terephthalate) and in particular PP (polypropylene). As will be discussed in details below, the fibers of the nonwoven for the bottom layer can comprise a melt additive that reduces the coefficient of friction of the nonwoven, in particular a fatty acid amid additive. The bottom layer is also typically not treated by a surfactant unlike the top layer of the core wrap.

Nonwoven fabrics (herein referred to as "nonwovens") are sheet or web structures bonded together by entangling fiber or filaments mechanically, thermally, or chemically. They are flat, porous sheets that are made directly from separate fibers. They are not made by weaving or knitting and do not require converting the fibers to yarn. Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

Spunbond, also called spunlaid, nonwovens are made in one continuous process. Fibers are spun through a number of small orifices in a spinneret to form fibers or filaments, which are then directly dispersed into a web by deflectors or can be directed with air streams on a moving foraminous surface, such as a wire mesh conveyor. Meltblown nonwovens are produced by extruding melted polymer fibers through a spinneret or die consisting of up to 40 holes per inch to form long thin fibers which are stretched and cooled by passing hot air over the fibers as they fall from the die. The diameters of the fiber is significantly reduced by hot air which also breaks the continuous filaments into microfibers of varying length to diameter ratio. The extremely fine fibers (typically polypropylene) differ from other extrusions, particularly spunbond, in that they have low intrinsic strength but much smaller size offering key properties.

The spunbond process can be combined with the meltblown process to form a multi-layer web having S (spunbond) layer and M (meltblown) layer, in particular SM, SMS or SMMS webs, which are strong and offer the intrinsic benefits of fine fibers. The nonwovens may be consolidated using known techniques, typically thermal point bonding. In thermal point bonding, heat is applied locally on individual regions of the nonwoven to locally melt and fuse the fibers together. Fusion bond patterns are for example disclosed in US 2011/0250413 (Hu et al.) and US2014/0072767A1 (Klaska et al.). The resultant web is typically collected into rolls at the supplier and subsequently converted to finished products.

Wrinkling

As indicated in the background, it is generally desirable to reduce the basis weight of the core wrap layers. While experimenting with core wrap layers both made with SMS nonwovens having a reduced basis weight of about 8 gsm, the present inventors have surprisingly found that a process anomaly known as wrinkling was more likely to happen at the top layer than at the bottom layer of the core wrap. Winkling can occur at the surface of a nonwoven when it is driven between two rollers on a converting line, and can lead to a fold-over that necessitate to stop the line. Both layers had the same composition and basis weight and were submitted to the same speed and tension. The difference between the top layer and the bottom layer was that the top layer had been treated by a surfactant to make it more hydrophilic, as is known in art.

While not wishing to be bound by theory, the present inventors believe that the wrinkle formation is caused by thin and thick spots in a web, due to difference in fiber orientation and basis weight variation. This is particularly a problem for low basis weight nonwovens such as those claimed. These irregularities can induce shear stress in the nonwoven in the converting line resulting in localized cross-machine direction (CD) buckling. These wrinkles can further develop in z-folds that force the line to stop or more desirably may resorb back to normal. This evolution is schematically illustrated in FIG. 7a-d.

Figure 7A:
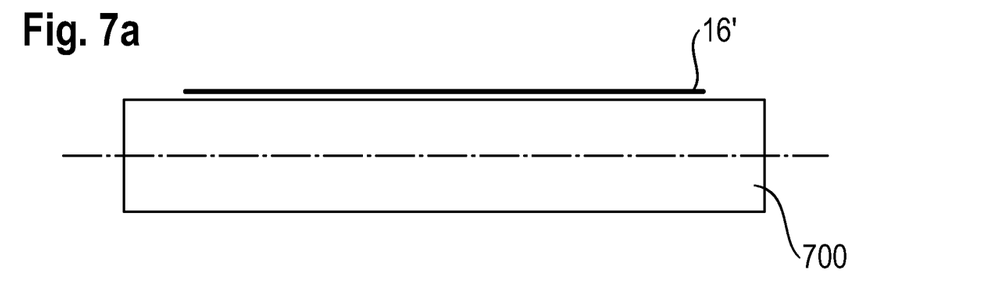
FIG. 7a, b, c, d illustrate the different stages of formation of a fold-over 730 for a nonwoven being driven on a cylindrical roller.

FIG. 7a shows a cross-section of a cylindrical roller 700 on top of which a continuous web of nonwoven 16' is driven at a given speed and tension. The nonwoven web is flat on the roller and is driven under optimal conditions.

Figure 7B:
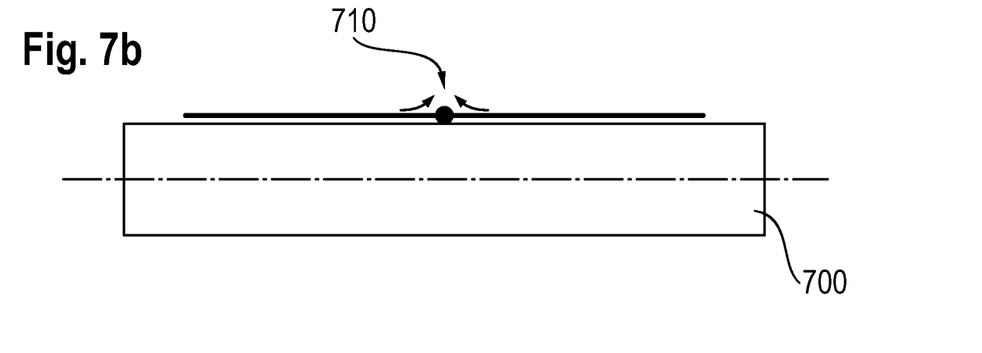

FIG. 7b illustrates the appearance of troughes, which are waves in the free span region between rollers of a cross-section of the web perpendicular to the direction of web flow, with flat or planar web where the web wraps around a roller. Troughing nearly always occurs on commercial converting line and is as such no concern.

Figure 7C:
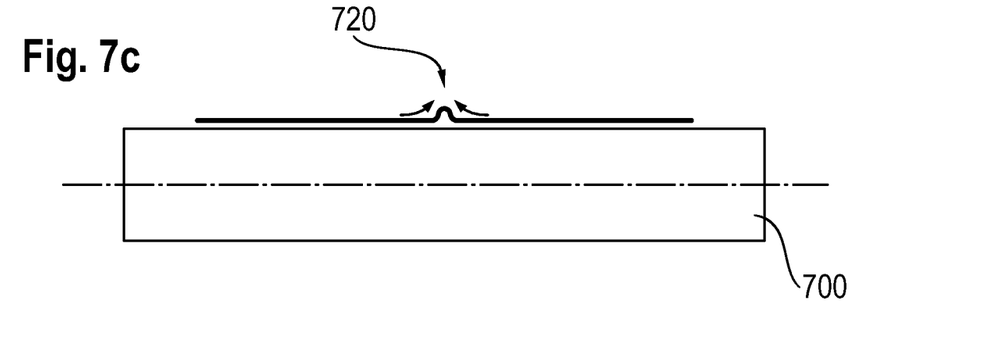

FIG. 7c illustrates the appearance of wrinkles that are developing from the troughes. Wrinkles are separations of the non-woven from the roller surface in a region where the web wraps around an idler. Wrinkles are typical of planar buckling due to compressive stresses which are substantially aligned with the cross-machine direction of a web.

Figure 7D:
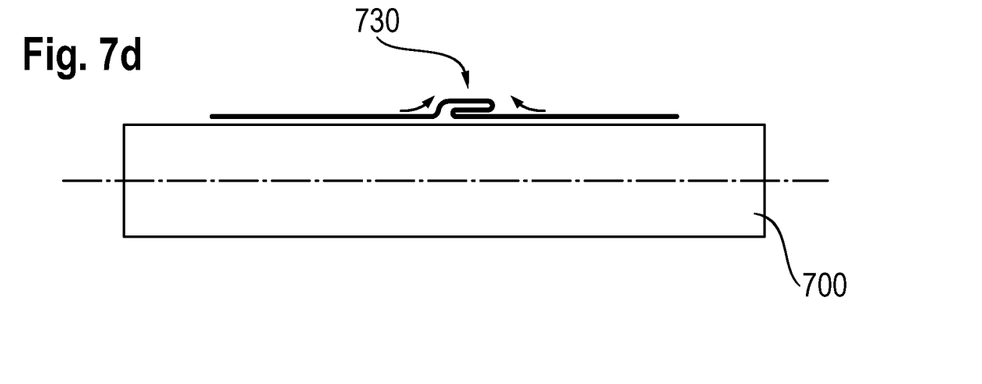

FIG. 7d illustrates next the development of a foldover, which is three or more layers of web in any one or more locations in the cross-machine direction, in the region where the web is wrapped around a roller. Foldover requires to stop the line to correct the issue.

Based on these findings, the inventors have hypothesized that bringing the Coefficient of Friction (CoF) of the bottom layer to the level of the top layer would lead to the same reduction of the wrinkles as in the top layer. While not wishing to be bound by theory, it is believed that the hydrophilic surfactant treatment had as a secondary effect a reduction of the CoF of the top layer. When the top layer is converted on the line, any wrinkles developing from troughes were found to flatten out quickly after their appearance. The CoF is traditionally used to measure the facility at which one layer can slide over another layer of the same material, and is measured according to the standard method ASTM D1894-01 with the further indications as indicated below. The lower the CoF is, the more the layers can slip over another. All values indicated herein are for the static CoF measured in the cross-machine (CD) direction of the nonwoven.

As will be shown below in the experimental section, the present inventors have indeed found that by adding a slip agent to the bottom layer, wrinkles can be efficiently prevented. The slip agent used may be in particular a melt additive comprising fatty acid amides. Fatty acid amides are known to migrate to the surface of the fibers of the nonwoven (effect known as blooming) and thereby reduce the coefficient of friction. As a further advantage, it is believed that the hydrophobic properties of the nonwoven are enhanced by the presence of the fatty acid amide. While the data presented were generated with a fatty acid amide melt additive, reducing the CoF of the nonwoven by other known means is also applicable, some of which will be discussed below.

CoF Reducing Agents—Fatty Acid Amides

The nonwovens of the present disclosure have a static coefficient of friction (CoF) as measured in cross-machine direction of no more than 0.40 (measured according to ASTM D1894-01), in particular from 0.20 to 0.39, more particularly from 0.25 to 0.38, more particularly from 0.30 to 0.38. This CoF can be in particular obtained by adding to the fibers of the nonwoven a melt additive that reduces the coefficient of friction of the nonwoven, or by any other known slip agent for reducing the CoF of a nonwoven, such as surface treatment with a slip agent. In addition to the bottom layer, the top layer of the core wrap can also advantageously have a CoF of no more than 0.40, in particular from 0.20 to 0.39, more particularly from 0.25 to 0.38, more particularly from 0.30 to 0.38.

Oleamide and erucamide are fatty acid amides commonly used as slip agent in polyethylene or polypropylene nonwovens. These compounds can be introduced as melt additives in the molten plastic before the making of the nonwovens. Oleamide is derived from mono-unsaturated C18 oleic acid, while erucamide is the amide of C22 mono-unsaturated erucic acid. The molecules of fatty acid amides are known to migrate at the surface of the fibers and thus provide a self-replenishing surface lubrication (effect referred to as "blooming"). This has been proven to reduce the coefficient of friction of the nonwovens made from these fibers or filaments. An early disclosure of this effect is disclosed in U.S. Pat. No. 3,454,519 (Hulse et al.), which discloses improved textile fibers prepared from isotactic polypropylene resin containing from about 0.01 to about 1.0% by weight of erucamide. Oleamide has a lower basis weight and is known to migrate to the film surface more rapidly than erucamide. Erucamide can however produce lower CoF values than equal quantities of Oleamide. Stearamide is also known to reduce the coefficient of friction when used as melt additive to the polymer melt used to make the nonwoven's fibers. Blend of such fatty acids may also be used. Such a blend of Stearamide and erucamide is for example disclosed in U.S. Pat. No. 6,740,609 (Peng et al.).

Typically the heat generated during the making of the nonwoven and on the diaper converting line may be enough for the blooming to occur. The migration of the molecules of fatty acid amides may also be accelerated up by heating the nonwoven at 40-50° C. for a few hours if necessary. The heat can be inserted via the thermo-bonding step as is commonly used in the production of nonwoven. Typically, the web is wound into rolls within a few seconds after the thermo-bonding step. Typically under these conditions a temperature of around 40° C. is maintained over several hours inside the rolls. It has been found that the insertion of an additional heating step, e.g. by using standard drying equipment (such as for drying surfactant coatings), does not only accelerate the blooming of erucamide but also enables an overall value of the coefficient of friction. This can be used for further usage reduction of erucamide. However, it requires an additional process operation which may not be available at the production line and its costs further energy. So it needs to be decided in each individual case if to insert an additional heating step for further erucamide usage level reduction.

Any fatty acid amide melt additives that can reduce the coefficient of friction of the nonwoven may be used. Suitable fatty acid amides include those derives from a mixture of C12-C28 fatty acids (saturated or unsaturated) and primary or secondary amines. A suitable example of a primary fatty acid amide includes those derived from a fatty acid and ammonia as illustrated in [1].

[1]

where R has a number of carbon atoms ranging from 11 to 27, in particular from 16 to 22 fatty acid. Fatty acid amides have the further advantage that they can increase the hydrophobicity and with this its barrier properties of the nonwoven, which is desirable for the bottom layer of the core wrap.

More generally, any treatment or melt additive that can reduce the CoF of the nonwoven may be used. Other suitable hydrophobic melt additives include hydrophobic silicones and ethoxylated fatty alcohols. Additional suitable hydrophobic melt additives are disclosed in US2016/067118 (Hammons et al.). A surfactant treatment as in for the top layer may also be envisioned to reduce the CoF of the bottom layer, however it may be desired that the bottom layer keep its barrier properties. The treatment or additive used to reduce to CoF may advantageously increase or at least maintain the barrier properties of the bottom layer of the core wrap. The hydrophobicity can be compared using the contact angle method, as indicated above. The top layer of the core wrap can be advantageously more hydrophilic than the bottom layer of the core wrap.

As will be illustrated below, the present disclosure allows to use low basis weight nonwovens as bottom layer for the core wrap, wherein the occurrence of wrinkles is diminished or avoided. This in turn ensures that foldover becomes even rare or is completely avoided under normal conditions.

It has also been found that a lower COF helps in the reduction of abrasion of small fibers (often referred to as "fuzz") from the nonwoven. Fuzz can impede the nonwoven's integrity and cause in-process contamination problems, besides an unpleasant visual appearance and haptic perception of the nonwoven. The unpleasant visual appearance of a nonwoven with significant fuzz may shine through the backsheet or the unpleasant haptic perception may be felt through the backsheet. Fuzz (loose small fibers) is generated due to abrasion in the converting process (in contact of the web with equipment parts, e.g. rollers, idlers, . . . ). This is a challenge particularly with low basis weight nonwovens which have an inherently lower strength and suffer more from in-process abrasion. It is believed that with a lower CoF, mechanically entangled filaments or fibers in the nonwoven are able to slide against each other when a force is applied on them rather than being plastically deformed until they tear. This enables in general more abrasion resistant NWs. The blooming of melt additives is known to be a thermodynamically driven process due to the incompatibility of the melt additive in the polymer matrix and happens very uniformly across all fibers in the web, as opposed to an in nature more inhomogeneous topical coating step applying a slip agent or lubricant onto the surface of the web. So the uniform blooming of the melt additive within all nonwoven layers to which it has been applied can enable a more effective reduction of fuzz creation.

Test Methods

Coefficient of Friction (CoF)

The Static Coefficient of Friction (CoF) is measured using ASTM Method D 1894-01 with the following particulars. The test is performed on a constant rate of extension tensile tester with computer interface (a suitable instrument is the MTS Insight using Testworks 4 Software, as available from MTS Systems Corp., Eden Prairie, Minn. or equivalent) fitted with a coefficient of friction fixture and sled as described in D 1894-01 (a suitable fixture is the Coefficient of Friction Fixture and Sled available from Instron Corp., Canton, Mass., or equivalent). The apparatus is configured as depicted in FIG. 1. c of ASTM 1894-01 using the same nonwoven substrate as the target surface and the sled surface. A load cell is selected such that the measured forces are within 10-90% of the range of the cell. The tensile tester is programmed for a crosshead speed of 127 mm/min, and a total travel of 130 mm. Data is collected at a rate of 100 Hz. All testing is performed in a room where the temperature is controlled at about 23° C.±2° C. and 50%±2% relative humidity with all samples and nonwoven targets conditioned under the same conditions for at least two (2) hours prior to testing.

The nonwoven is harvested from the absorbent article using cryogenic freeze spray (e.g., Cyto-Freeze available from VWR) or other appropriate means to separate the layers. Ensure that the orientation of the test specimen is maintained, i.e., cross direction CD versus machine direction MD, and embossed surface versus non-embossed surface if applicable. Cut a test specimen 8.9 cm by 8.9 cm from the sample substrate with its cut sides parallel and perpendicular to the machine direction of the substrate. Mount the specimen onto the foam rubber side of the sled by wrapping the edges around to the back of the sled and securing with adhesive tape. The specimen is oriented such that the specimen will be pulled along the cross direction CD of the specimen during the test and that the embossed surface is directed toward the target surface.

For the nonwoven target, cut a specimen approximately 8.0 cm by 20.0 cm with the substrate oriented such that the cross direction CD is parallel with the direction of the sled pull and the embossed surface is facing the sled's surface. The nonwoven target is secured to the platform using masking tape around its circumference such that the no tape interferes with the movement of the sled during testing. A new nonwoven target and sled surface is used for each measurement.

Set up the tensile test as described above. Zero the load cell and crosshead. Connect the sled to the lead line and place the sled, specimen surface down, onto the target plane. The line should be secure under the pulley and taut, with less than 1.0 g force on the load cell. Start the test and collect force verses distance data. When the test is complete, remove the specimen from the sled and target. From the resulting extension (mm) versus force (gf) graph calculate the Static and Kinetic Coefficient of Friction as follows:

Static CoF=maximum peak force (gf) for the initial peak divided by the measured mass (g) of the sled and recorded to the nearest 0.01.

The test is repeated for a total of ten (10) replicates. Average values are calculated separately for Static CoF for each of the specified targets and reported to the nearest 0.01 units.

SEM Method for Determining Contact Angle on Fibers

A rectangular specimen measuring 1 cm×2 cm is cut from the middle of the material to be tested with the length of the specimen (2 cm) aligned with a longitudinal centerline of the article. The specimen is handled gently by the edges using forceps and is mounted flat with the skin-facing side up on an SEM specimen holder using double-sided tape. The specimen is sprayed with a fine mist of water droplets generated using a small hobby air-brush apparatus. The water used to generate the droplets is distilled deionized water with a resistivity of at least 18 Me-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the images taken as is known in the art. Twenty separate droplets are imaged from which forty contact angle measurements are performed (one on each side of each imaged droplet), and the arithmetic average of these forty contact angle measurements is calculated and reported as the contact angle for that specimen.

Experimental

Test Nonwovens

Different nonwovens (NW) having the same SMMS laminate structure and same 8 gsm basis weight were made using a conventional process as is known in the art. The spun to melt weight ratio was around 80/20. Thermal bonds were applied via a heated calendering roll to the nonwovens as is known in the art. A commercially available oval bond pattern (Ungrich U2888) was used. The reference nonwoven was not further treated. One nonwoven was hydrophillically treated by a surfactant as would be done for a top layer of the core wrap. The other nonwovens had different amount of erucamide introduced as hot melt additive in the S layers at 0.1%, 0.3% and 0.5% by weight of the SMMS nonwoven. The Erucamide was added by extrusion through a 10% masterbatch containing 10% of active Erucamide. The Erucamide was added into both S-beams. The weight percentage of the hotmelt additive refers to the total mass of the NW.

The static CoF in CD direction were measured on 10 randomly selected samples for each nonwoven. The mean and the standard variation values are reported below.

| | Mean | Std Deviation |
|---|---|---|
| Reference (no surfactant, no erucamide) | 0.51 | 0.069 |
| Reference with a surfactant treatment | 0.385 | 0.019 |
| Reference + 0.1% Erucamide | 0.394 | 0.031 |
| Reference + 0.3% Erucamide | 0.329 | 0.019 |
| Reference + 0.5% Erucamide | 0.341 | 0.033 |

It is known that some heat introduction is advantageous for the blooming of erucamide out of PP fibers (typically a few hours at 40° C.). However, no additional heat treatment in the test nonwovens was found necessary for the erucamide to bloom out at the surface of the fibers, presumably due to the stored heat in the calendering roll. In production processes, enough heat can also be provided via the thermo-bonding (calendering) step of the NW and subsequent winding of the NW on rolls whereby residual process heat is stored inside the rolls.

As can be seen above, already introducing 0.1% Erucamide was found to be sufficient to lower the CoF of the bottom layer to about the same level as a hydrophillically treated nonwoven that can be used as top layer.

0.3% Erucamide was found to lower even more the CoF. Increasing further the level of Erucamide to 0.5% by weight did not further decrease the CoF significantly in this experiment.

Figure 8:
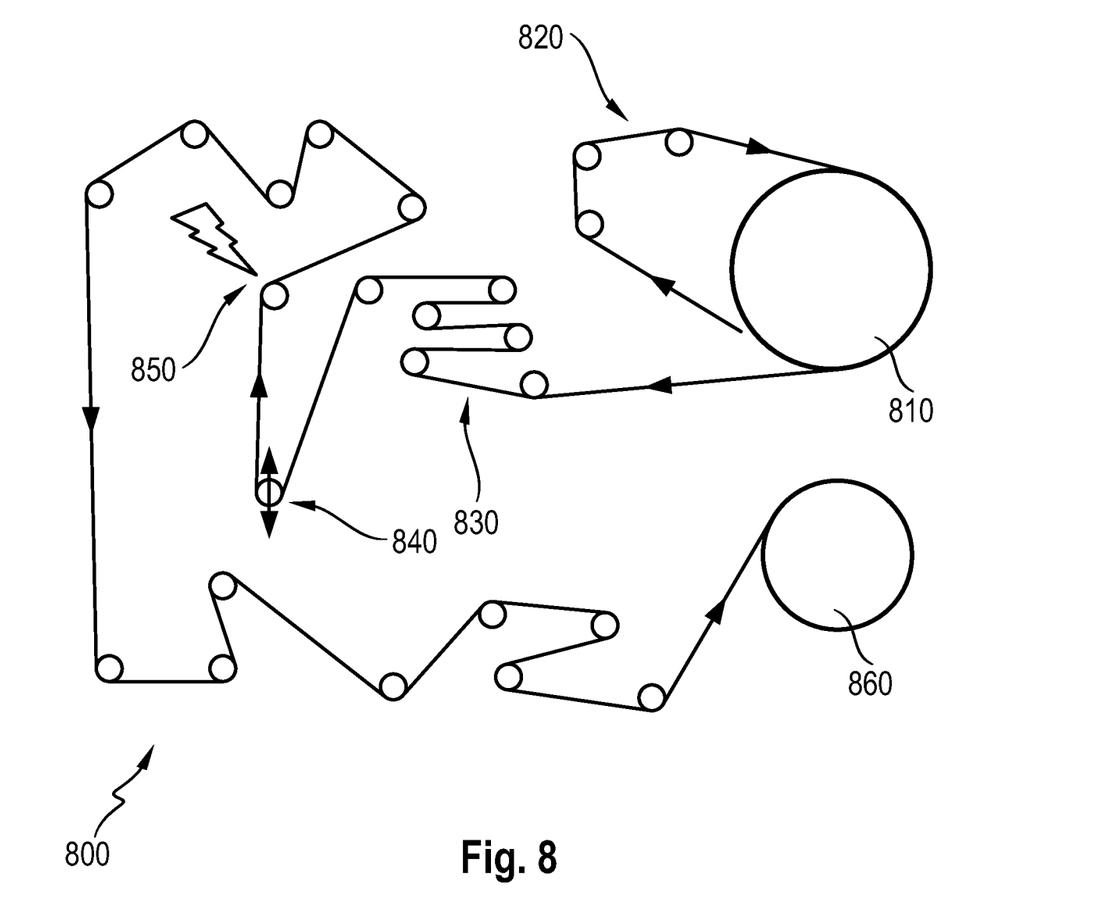
FIG. 8 is a schematic representation of the test stand used in the experimental section.

Test Stand:

The 8 gsm SMMS untreated reference nonwoven (NW) and the inventive 8 gsm SMMS NW containing 0.3% erucamide were tested on a static test stand that simulates a portion of a diaper converting line. The test stand 800 is schematically represented on FIG. 8, with the following reference numbers indicated the following elements:

810=roll of the nonwoven to be tested,
820=idlers that loop the web back over the unwind roll,
830=dancer to control tension
840=Idler roll on a linear stage (the distance between 840 and 850 is the webspan and can be varied, the web tension is also between these two idlers),
850=Test idler (a concave idler was used in this study) observed by a camera (represented by the lighting) to analyze the presence and formation of wrinkles and other anomaly,
860=wind-up roll.

The 3-idlers system 820 lessen any wound up tensions prior to going into the dancer 830 that has the two idlers on the left able to swing. The concave idler 850 used in the test design had a V-shape concavity (with a diameter of 50 mm at the edges and a depth of the valley of 800 μm, i.e. a diameter of (50 mm-2*800 μm) in the center). Before the wind-up roll 860, the web path can also use a dancer similar to 830 to control tension (not represented in FIG. 8) in the rewinding.

Different typical tensions and web spans, which play a role in production processes, e.g. in a splicing unit in the production line, were tested. The presence or absence of wrinkles was recorded with a camera on top of the idler (this test stand did not mimic the actual—dynamic—splicing process, during which tensions and web spans are ramping up and down, but represents static corner points of a splicing process). The absence of "wrinkles" is indicative of a smooth conversion in production processes, particularly during the splicing step, while the presence of wrinkles is indicative of convertibility problems production processes, particularly during the splicing step. Convertibility problems occur when wrinkles grow into fold-overs which are irreversible and ultimately cause line stops.

Definitions

Troughing: Waves in the free span region between rollers of a cross-section of the web perpendicular to the direction of web flow, with flat or planar web where the web wraps around a roller. Troughing nearly always occurs and is as such no concern.

Wrinkling: Separation of the non-woven from the roller surface in a region where the web wraps around an idler. Typical of planar buckling due to compressive stresses which are substantially aligned with the cross-machine direction of a web.

Foldover: Three or more layers of web in any one or more locations in the cross-machine direction, in the region where the web is wrapped around a roller.

Test Results

| Set Tension [N] | Set Webspan [mm] | Web Material | Observation |
|---|---|---|---|
| 7.4 (±1.4) | 720 | Inventive NW (0.3% Erucamide) | Troughing |
| 3.5 (±1.1) | 1100 | Inventive NW (0.3% Erucamide) | Troughing |
| 7.4 | 1100 | Inventive NW (0.3% Erucamide) | Troughing |
| 3.5 | 720 | Inventive NW (0.3% Erucamide) | Troughing |
| 7.4 | 720 | Reference NW | Wrinkling |
| 3.5 | 1100 | Reference NW | Wrinkling |
| 7.4 | 1100 | Reference NW | Wrinkling |
| 3.5 | 720 | Reference NW | Wrinkling |

Whenever "wrinkling" was reported, 1 to 2 discrete wrinkle formation events where observed within a time span of 10 s, when looking (with the camera) at the idler.

Packages

Absorbent articles for personal hygiene are typically packaged by the manufacturer in a plastic bag and/or a cardboard box for transport and sale. The articles may also be folded before being packaged to save space as is known in the art. The back and front ears of taped diapers are for example typically folded inwardly before bi-folding the diaper along its transversal axis before being packaged. The absorbent articles may be packaged under compression, so as to reduce the size of the package so that the caregivers can easily handle and store the packages, while also providing distribution and inventory savings to manufacturers owing to the size of the packages. The package may for example comprise from 2 to 200 of the articles.

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular forms of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a liquid permeable topsheet;
a liquid impermeable backsheet; and
an absorbent core at least partially between the topsheet and the backsheet,
wherein the absorbent core comprises an absorbent material enclosed in a core wrap comprising a top layer and a bottom layer, wherein the top layer comprises a surfactant to increase hydrophilicity of the top layer, wherein the bottom layer of the core wrap comprises a nonwoven comprising synthetic fibers, wherein the nonwoven has a basis weight from about 6 $g/m^2$ to about 10 $g/m^2$, wherein the fibers of the nonwoven comprise a slip agent that reduces a static coefficient of friction of the nonwoven, and wherein the static coefficient of friction of the nonwoven matches a static coefficient of friction of the top layer.

2. The absorbent article according to claim 1, wherein the slip agent is a melt additive.

3. The absorbent article according to claim 2, wherein the melt additive is a fatty acid amide.

4. The absorbent article according to claim 3, wherein the fatty acid amide is selected from Oleamide, Erucamide, Stearamide and mixtures thereof.

5. The absorbent article according to claim 3, wherein the nonwoven comprises more than 0.05% of the fatty acid amide, by weight of the nonwoven.

6. The absorbent article according to claim 5, wherein the nonwoven comprises more than 0.1% of the fatty acid amide, by weight of the nonwoven.

7. The absorbent article according to claim 3, wherein the nonwoven comprises less than 1% of the fatty acid amide, by weight of the nonwoven.

8. The absorbent article according claim 7, wherein the nonwoven comprises up to 0.6% of the fatty acid amide, by weight of the nonwoven.

9. The absorbent article according to claim 3, wherein the nonwoven is a multilayer nonwoven comprising at least one spunbond layer and at least one meltblown layer, and wherein the spunbond layer comprises the fatty acid amide.

10. The absorbent article according to claim 9, wherein the nonwoven is a SMS or SMMS nonwoven.

11. The absorbent article according to claim 1, wherein the nonwoven comprises from about 0.2% to about 0.5% of erucamide, by weight of the nonwoven.

12. The absorbent article according to claim 1, wherein the top layer of the core wrap is a second nonwoven having a second basis weight from about 6 $g/m^2$ to about 10 $g/m^2$.

13. A process for making an absorbent core, wherein the process comprises:
adding a melt additive to a plastic melt, wherein the melt additive is a coefficient of friction reduction agent;
making a nonwoven comprising fibers from the plastic melt;
converting the nonwoven in a continuous process on a converting line into a portion of the absorbent core, wherein the nonwoven is used to form a bottom layer of a core wrap of the absorbent core, the absorbent core comprising an absorbent material and a top layer, the top layer and the bottom layer forming the core wrap around the absorbent material; and
treating the top layer with a surfactant to increase a hydrophilicity of the top layer and such that a static coefficient of friction of the nonwoven matches a static coefficient of friction of the top layer.

14. The process according to claim 13, comprising:
heat treating the nonwoven so that diffusion of the melt additive at a surface of the fibers of the nonwoven is accelerated and the coefficient of friction is further reduced.

15. An absorbent article having a wearer-facing surface, the absorbent article comprising:
a liquid permeable topsheet;
a liquid impermeable backsheet; and
an absorbent core at least partially between the topsheet and the backsheet,
wherein the absorbent core comprises an absorbent material enclosed in a core wrap comprising a first layer and a second layer, wherein the first layer is positioned more proximate to the wearer-facing surface than the second layer, wherein the second layer of the core wrap comprises a nonwoven comprising synthetic fibers, wherein the nonwoven has a basis weight from about 6 $g/m^2$ to about 10 $g/m^2$, wherein the first layer and the nonwoven have a static coefficient of friction as measured in cross-machine direction of no more than 0.40, as measured according to ASTM D1894-01, and wherein at least some of the fibers of the nonwoven comprise a slip agent that reduces the static coefficient of friction of the nonwoven.

16. The absorbent article according to claim 15, wherein the slip agent is a melt additive.

17. The absorbent article according to claim 16, wherein the nonwoven is a SMS or SMMS nonwoven.

18. The absorbent article according to claim 17, wherein the first layer of the core wrap is a second nonwoven having a basis weight from about 6 $g/m^2$ to about 10 $g/m^2$ and comprises a surfactant to increase its hydrophilicity.

* * * * *